(12) United States Patent
Mayo

(10) Patent No.: US 9,364,633 B2
(45) Date of Patent: Jun. 14, 2016

(54) EXHALED VAPOR COLLECTION DEVICE

(71) Applicant: Jesse Mayo, Kingston, GA (US)

(72) Inventor: Jesse Mayo, Kingston, GA (US)

(*) Notice: Subject to any disclaimer, the term of this patent is extended or adjusted under 35 U.S.C. 154(b) by 0 days.

(21) Appl. No.: 14/499,137

(22) Filed: Sep. 27, 2014

(65) Prior Publication Data

US 2015/0013680 A1    Jan. 15, 2015

(51) Int. Cl.
| | | |
|---|---|---|
| *A61M 16/08* | (2006.01) | |
| *A62B 18/02* | (2006.01) | |
| *A62B 18/10* | (2006.01) | |
| *G06F 13/00* | (2006.01) | |
| *G06K 19/00* | (2006.01) | |

(52) U.S. Cl.
CPC ............ *A61M 16/0808* (2013.01); *A62B 18/02* (2013.01); *A62B 18/10* (2013.01); *G06F 13/00* (2013.01); *G06K 19/00* (2013.01)

(58) Field of Classification Search
CPC ... A61M 16/0808; A61B 5/097; A62B 9/003; A62B 18/025
USPC ............ 128/204.16; 55/428.1; 141/82, 86, 98
See application file for complete search history.

(56) References Cited

U.S. PATENT DOCUMENTS

| | | | | | |
|---|---|---|---|---|---|
| 1,648,438 | A | * | 11/1927 | Armbrust .................. | C02F 1/18 128/204.16 |
| 3,968,812 | A | * | 7/1976 | Eross ................ | A61M 16/0808 128/205.12 |
| 4,038,698 | A | | 8/1977 | Smith | |
| 4,417,574 | A | * | 11/1983 | Talonn .............. | A61M 16/0808 128/205.12 |
| 4,620,537 | A | * | 11/1986 | Brown ................. | A62B 18/025 128/201.13 |
| 4,622,964 | A | * | 11/1986 | Flynn ................ | A61M 16/0078 128/205.24 |
| 4,683,869 | A | | 8/1987 | Wilcox | |
| 5,101,821 | A | * | 4/1992 | Carie, Jr. ................ | A62B 9/003 128/205.12 |
| 5,357,947 | A | * | 10/1994 | Adler ................. | A41D 13/1146 128/201.13 |
| 5,435,299 | A | * | 7/1995 | Langman ............... | A62B 9/003 128/201.13 |
| 5,490,501 | A | | 2/1996 | Crowley | |
| 5,924,995 | A | * | 7/1999 | Klein .................... | A61B 5/0836 600/531 |
| 6,415,453 | B1 | * | 7/2002 | Anderson ............ | A62B 17/005 165/46 |
| 6,883,185 | B2 | | 4/2005 | Duncan | |
| 7,810,493 | B2 | | 10/2010 | Resnick | |
| 7,958,888 | B2 | | 6/2011 | Wagner, III | |
| 8,220,664 | B1 | | 7/2012 | Teetzel et al. | |
| 8,313,440 | B2 | * | 11/2012 | Friedman ............... | A61B 5/097 600/529 |

* cited by examiner

*Primary Examiner* — Timothy L Maust
(74) *Attorney, Agent, or Firm* — Crose Law LLC; Bradley D. Crose

(57) ABSTRACT

A collection device for exhaled vapor is provided. The exhaled vapor collection device collects a wearer's exhalant to provide for later hydration. In at least one embodiment, the collection device for exhaled vapor includes a facial mask; a one-way intake valve disposed within the facial mask and configured to allow the one-way intake of air into the facial mask; an exit port disposed within the facial mask and configured to allow the one-way exit of air out from the facial mask; a proximal condensation tube fluidly coupled to the exit port of the facial mask, an interior surface upon which exhaled vapor collects; and a collection bag tube fluidly coupled to the condensation tube to collect a wearer's exhalant. The exhaled vapor collection device is configured to collect a wearer's exhalant in the collection bag to provide for later hydration.

14 Claims, 11 Drawing Sheets

EXHALED VAPOR COLLECTION DEVICE

FIELD OF THE INVENTION

The technology described herein relates generally to water collection devices, personal hydration devices, and breath transfer devices. More specifically, this technology relates to an exhaled vapor collection device to collect a wearer's exhalant to provide for later hydration.

BACKGROUND OF THE INVENTION

Water is essential to life. It is a vital nutrient helpful to every part and function of the human body. Adequate hydration is necessary to maintain healthy mental and physical performance. For example, water aids the body in performing its digestive, circulatory, absorption, and excretory functions. Without the appropriate levels of hydration, the body will not perform these functions properly. Water constantly must be added to the body. Without doing so, dehydration becomes a serious concern.

Dehydration occurs when the human body does not have as much water and fluids in it as it should to maintain bodily functions. Dehydration is caused by too much output of water and bodily fluids with too little intake of water and fluids. Left unchecked, dehydration can escalate quickly into severe dehydration. Severe dehydration is a life-threatening emergency.

Related utility patents known in the art include the following:

U.S. Pat. No. 4,683,869, issued to Wilcox on Aug. 4, 1987, discloses a breath transfer device.

U.S. Pat. No. 7,958,888, issued to Wagner, III on Jun. 14, 2011, discloses a circulation apparatus and method.

U.S. Pat. No. 6,883,185, issued to Duncan on Apr. 26, 2005, discloses a survival suit.

U.S. Pat. No. 6,415,453, issued to Anderson et al. on Jul. 9, 2002, discloses a low temperature thermal insulation garment utilizing the wearer's exhalant.

U.S. Pat. No. 4,038,698, issued to Smith on Apr. 2, 1977, discloses a one-piece rainsuit and face mask.

U.S. Pat. No. 5,490,501, issued to Crowley on Feb. 13, 1996, discloses an avalanche victim's air-from-snow breathing device.

U.S. Pat. No. 4,417,574, issued to Talonn et al. on Nov. 29, 1983, discloses a liquid drain for a patient breathing apparatus.

U.S. Pat. No. 8,220,664, issued to Teetzel et al. on Jul. 17, 2012, discloses a powered hydration system.

U.S. Pat. No. 7,810,493, issued to Resnick on Oct. 12, 2010, discloses drink tube system for a respiratory protective device.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a exhaled vapor collection device to collect a wearer's exhalant to provide for later hydration.

In one exemplary embodiment, the technology described herein provides an exhaled vapor collection device to collect a wearer's exhalant to provide for later hydration, wherein the device includes: a facial mask; a one-way intake valve disposed within the facial mask and configured to allow the one-way intake of air into the facial mask; an exit port disposed within the facial mask and configured to allow the one-way exit of air out from the facial mask; a proximal condensation tube fluidly coupled to the exit port of the facial mask, an interior surface upon which exhaled vapor collects; and a collection bag tube fluidly coupled to the proximal condensation tube to collect a wearer's exhalant. The exhaled vapor collection device is configured to collect a wearer's exhalant in the collection bag to provide for later hydration.

In at least one embodiment, the exhaled vapor collection device also can include a pair of one-way intake valves disposed within the facial mask and configured to allow the one-way intake of air into the facial mask.

In at least one embodiment, the exhaled vapor collection device further can include a plurality of proximal condensation tubes fluidly coupled to the exit port of the facial mask, each proximal condensation tube having an interior surface upon which exhaled vapor collects.

In at least one embodiment, the exhaled vapor collection device also can include a pressure escape valve fluidly coupled to the proximal condensation tube and configured for operative actuation to release pressure.

In at least one embodiment, the exhaled vapor collection device further can include a distal condensation tube to facilitate greater vapor collection.

In at least one embodiment, the exhaled vapor collection device also can include a distal condensation tube fluidly coupled to the proximal condensation tube to facilitate greater vapor collection.

In at least one embodiment, the exhaled vapor collection device further can include a distal condensation tube fluidly coupled to the proximal condensation tube and disposed with the collection bag to facilitate greater vapor collection with a greater tube surface area.

In at least one embodiment, the exhaled vapor collection device also can include a plurality of distal condensation tubes fluidly coupled to the proximal condensation tube and disposed with the collection bag to facilitate greater vapor collection with a greater tube surface area.

In at least one embodiment, the exhaled vapor collection device also can include an elongated distal condensation tube disposed with the collection bag having a plurality of curves and a plurality of direction changes within the collection bag to facilitate greater vapor collection with a greater tube surface area.

In at least one embodiment, the exhaled vapor collection device also can include a plurality of pores disposed within a surface of the distal condensation tube to facilitate greater vapor collection.

In at least one embodiment, the exhaled vapor collection device also can include a sponge disposed with the collection bag to facilitate greater vapor collection.

In at least one embodiment, the exhaled vapor collection device also can include a strap disposed on the facial mask to wrap around a back side of the wearer's head and secure the mask to the wearer over both the nose and the mouth of the wearer.

In yet another exemplary embodiment, the exhaled vapor collection device to collect a wearer's exhalant to provide for later hydration includes: a facial mask; at least one one-way intake valve disposed within the facial mask and configured to allow the one-way intake of air into the facial mask; an exit port disposed within the facial mask and configured to allow the one-way exit of air out from the facial mask; at least one proximal condensation tube fluidly coupled to the exit port of the facial mask, an interior surface upon which exhaled vapor collects; a collection bag tube fluidly coupled to the condensation tube to collect a wearer's exhalant; and at least one distal condensation tube disposed within the collection bag to facilitate greater vapor collection. The exhaled vapor collection device is configured to collect a wearer's exhalant in the collection bag to provide for later hydration.

In yet another exemplary embodiment, the exhaled vapor collection device to collect a wearer's exhalant to provide for later hydration includes: a facial mask; a strap disposed on the facial mask to wrap around a back side of the wearer's head and secure the mask to the wearer over both the nose and the mouth of the wearer; a pair of one-way intake valves disposed within the facial mask and configured to allow the one-way intake of air into the facial mask; an exit port disposed within the facial mask and configured to allow the one-way exit of air out from the facial mask; a plurality of proximal condensation tubes fluidly coupled to the exit port of the facial mask, each proximal condensation tube having an interior surface upon which exhaled vapor collects; a collection bag tube fluidly coupled to the condensation tube to collect a wearer's exhalant; a plurality of distal condensation tubes fluidly coupled to the proximal condensation tube and disposed with the collection bag to facilitate greater vapor collection with a greater tube surface area; and a pressure escape valve fluidly coupled to the proximal condensation tube and configured for operative actuation to release pressure. The exhaled vapor collection device is configured to collect a wearer's exhalant in the collection bag to provide for later hydration.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Figure 1:
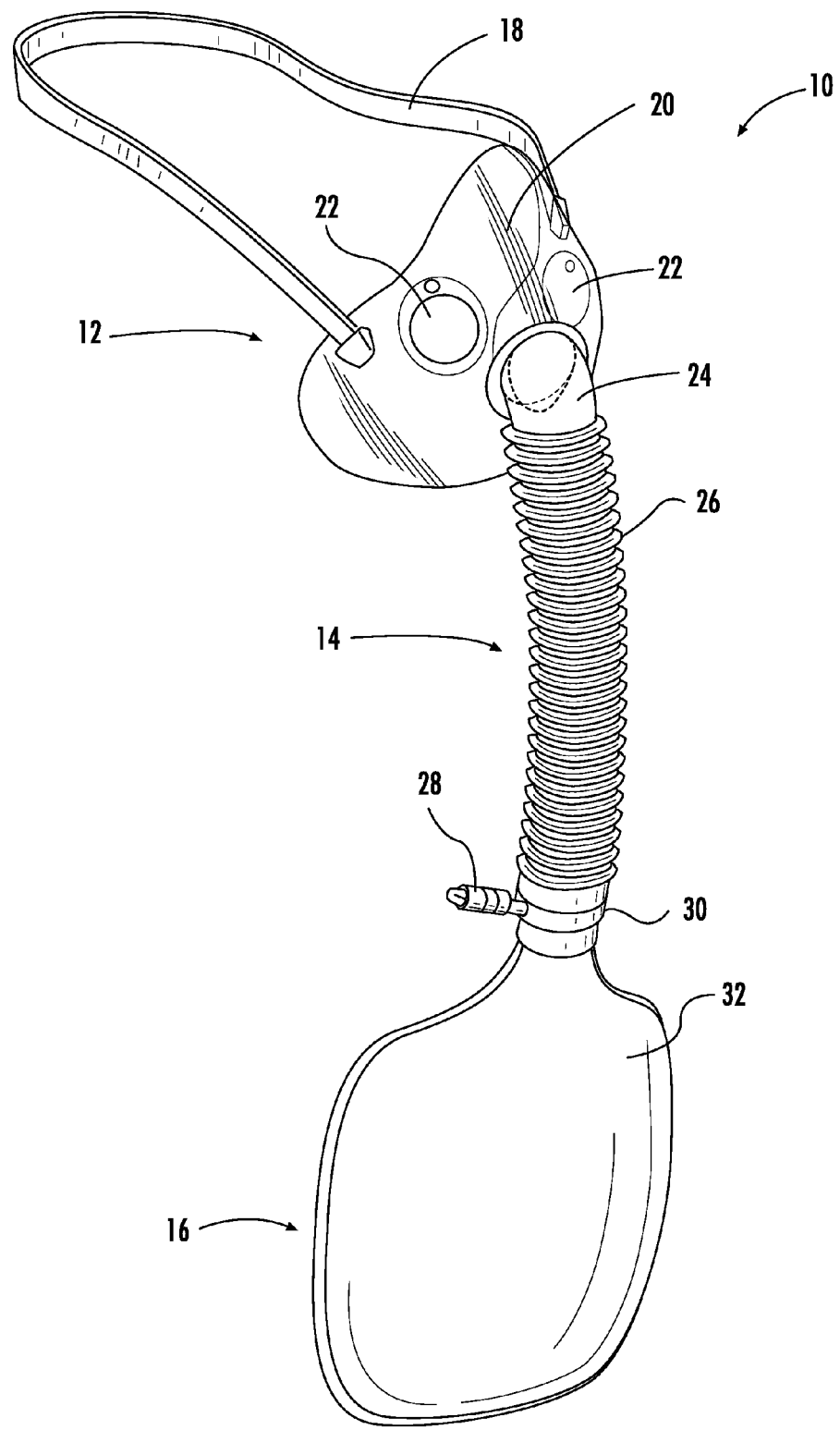
FIG. 1 is a front perspective view of an exhaled vapor collection device, according to an embodiment of the technology described herein.

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides an exhaled vapor collection device to collect a wearer's exhalant to provide for later hydration. The exhaled vapor collection device can be used, for example, as a combined hydration device and survival device for hikers and the like. The exhaled vapor collection device captures exhaled vapor that would otherwise be lost or wasted.

Referring now to the Figures, an exhaled vapor collection device 10 is shown. The exhaled vapor collection device 10 is configured to collect a wearer's exhalant to provide for later hydration. It is know that in a survival situation, one may go perhaps for about three days before the lack of hydration becomes fatal. The specific time may vary based on many factors, but three days is a commonly known and stated estimate for survival. The exhaled vapor collection device 10 is configured such that the wearer can collect exhaled vapor, use the condensed water for hydration, and thus extend the number of days one might endure without additional hydration.

The collected vapor/water is that which would be normally lost without such an exhaled vapor collection device 10.

The exhaled vapor collection device 10 includes a facial mask 12. The facial mask 12 is configured to cover the wearer of the exhaled vapor collection device 10 over both the nose and the mouth of the wearer's face with an outer shell 20. The outer shell is flexible. With this application of the facial mask 12, the wearer may breathe inwardly in a normal fashion, and exhale outwardly such that the wearer's exhalant is collected in the exhaled vapor collection device 10. The outer shell 20 is generally clear to allow visibility through the facial mask 12. The outer shell 20 can be manufactured of a lightweight plastic product for ease of use and comfort. The facial mask 12, as well as other subcomponents of the exhaled vapor collection device 10 are interchangeable, and can be swapped or replaced.

To aid in the application of the face mask 12, a secure strap 18 is provided. The strap 18 is coupled to the facial mask 12 at two or more points. The strap 18 is adjustable to accommodate varied sizes of the wearer and for comfort. The facial mask 12 strap 18 is configured to wrap around a back side of the wearer's head and secure the facial mask 12 to the wearer over both the nose and the mouth of the wearer. The strap can be made of plastic, nylon, rubber, or the like such that it is flexible and provides comfort to the wearer.

The facial mask 12 includes at least one one-way intake valve 22 disposed within the facial mask 12. The one-way intake valve 22 is configured to allow for only the one-way intake of air into the facial mask 12. The one-way intake valve 22 precludes exit air through the intake passageway. As depicted in the Figures, a pair of one-way intake valves 22 are disposed within the facial mask 12 and configured to allow the one-way intake of air into the facial mask 12.

Each one-way intake valve 22 includes a valve flap 21. The valve flap 21 is configured such that air may be taken in, but not pushed out through the same intake-only valve. As such all air breathed out from the wearer through the facial mask 12 is precluded from exit via the one-way intake valve 22, but rather must be exited through an exit port 24 defined for that purpose.

The exit port 24 is disposed within the facial mask 12. The exit port 24 is configured to allow the one-way exit of air out from the facial mask 12 and to be forwarded through the remainder of the exhaled vapor collection device 10. The exit port 24 is further configured as a coupler to fluidly couple the facial mask 12 with a proximal condensation tube assembly 14.

Figure 2:
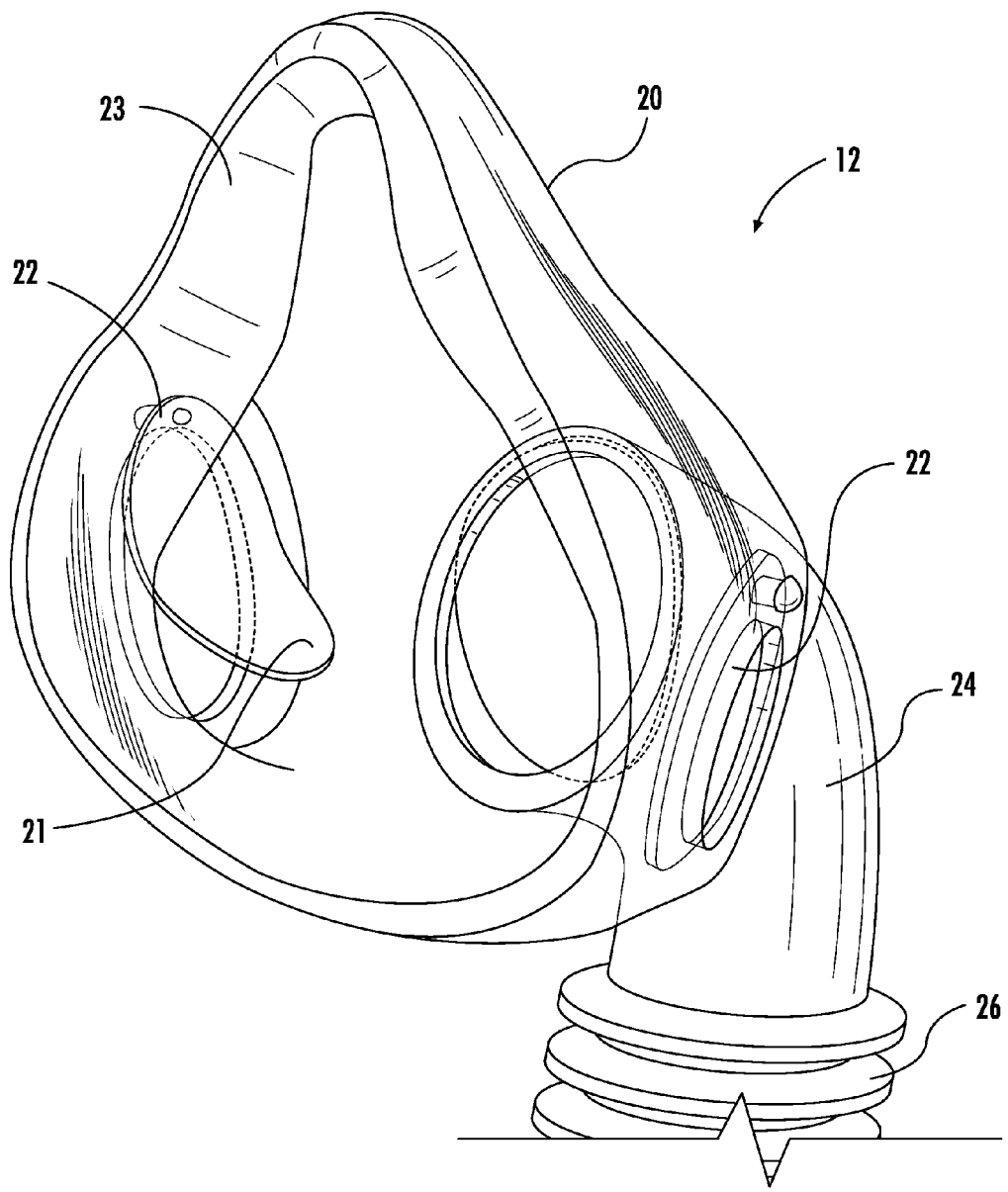
FIG. 2 is a perspective, close up view of the facial mask and intake valves depicted in FIG. 1.

In at least one embodiment, the facial mask 12 includes an air pillow 23, as depicted best in FIG. 2. The air pillow 23 can be integrally formed with the facial mask 12. The air pillow 23 provides for increased comfort of the facial mask 12 upon the face of the wearer. The air pillow 23 contours to the facial lines of the wearer and increases the seal effect to reduce lost air flow, while at the same time providing a comfort fit to the wearer.

The facial mask 12 is fluidly coupled to a proximal condensation tube assembly 14. The proximal condensation tube assembly 14 includes at least one proximal condensation tube 26. The proximal condensation tube 26 is fluidly coupled to the exit port 24 of the facial mask. The proximal condensation tube 26 provides an interior surface upon which exhaled vapor collects and can thereby subsequently collects and drip into a collection bag assembly 16.

Figure 4:
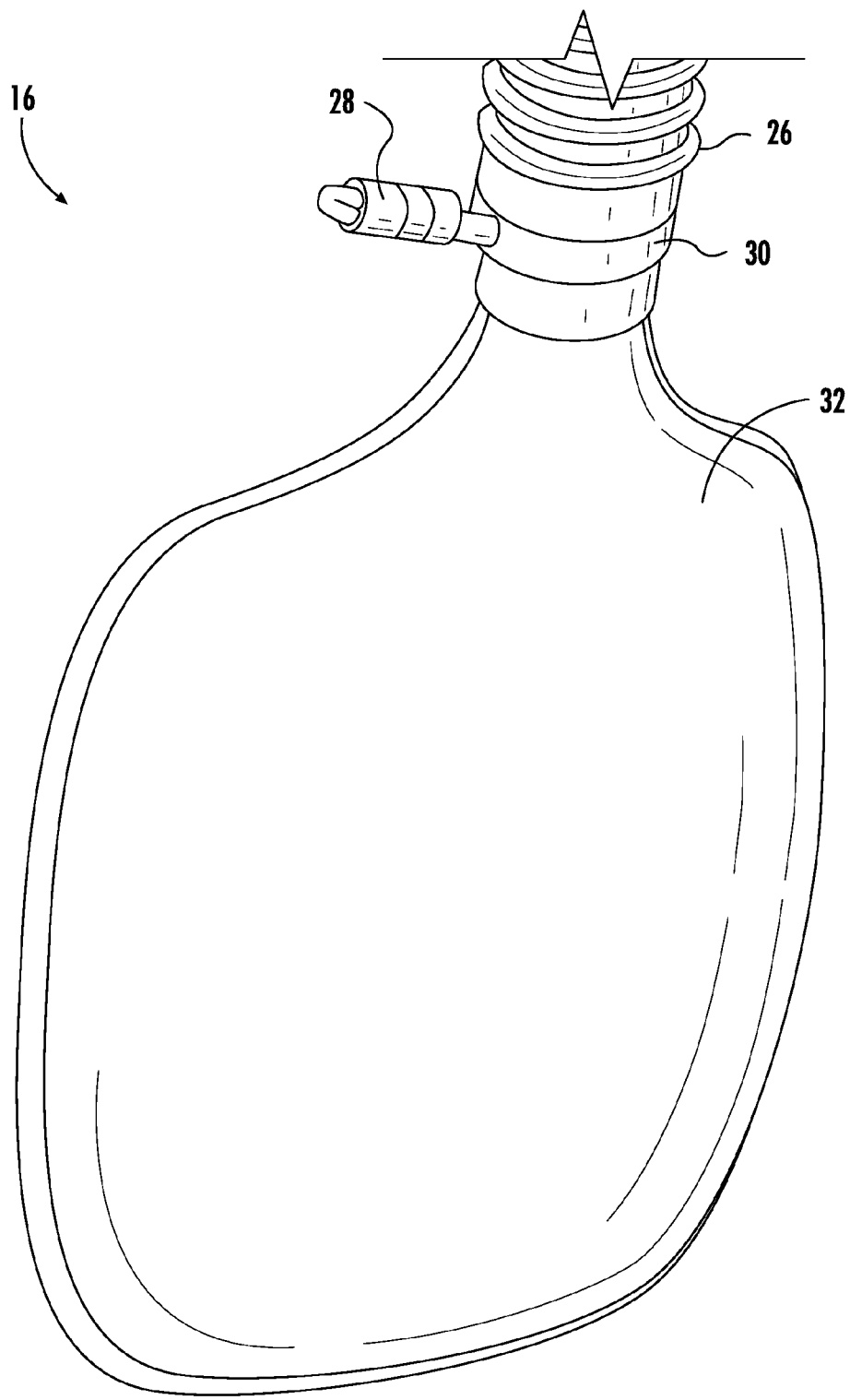
FIG. 4 is a perspective, close up view of the collection bag depicted in FIG. 1.

The exhaled vapor collection device 10 includes a collection bag assembly 16. The collection bag assembly 16 includes at least a collection bag 32. The collection bag 32 itself is best depicted in FIG. 4. The collection bag assembly 16 is fluidly coupled to the proximal condensation tube assembly 14. The means by which to couple the collection bag assembly 16 to the proximal condensation tube assembly 14 can include coupler valve 30.

Figure 11:
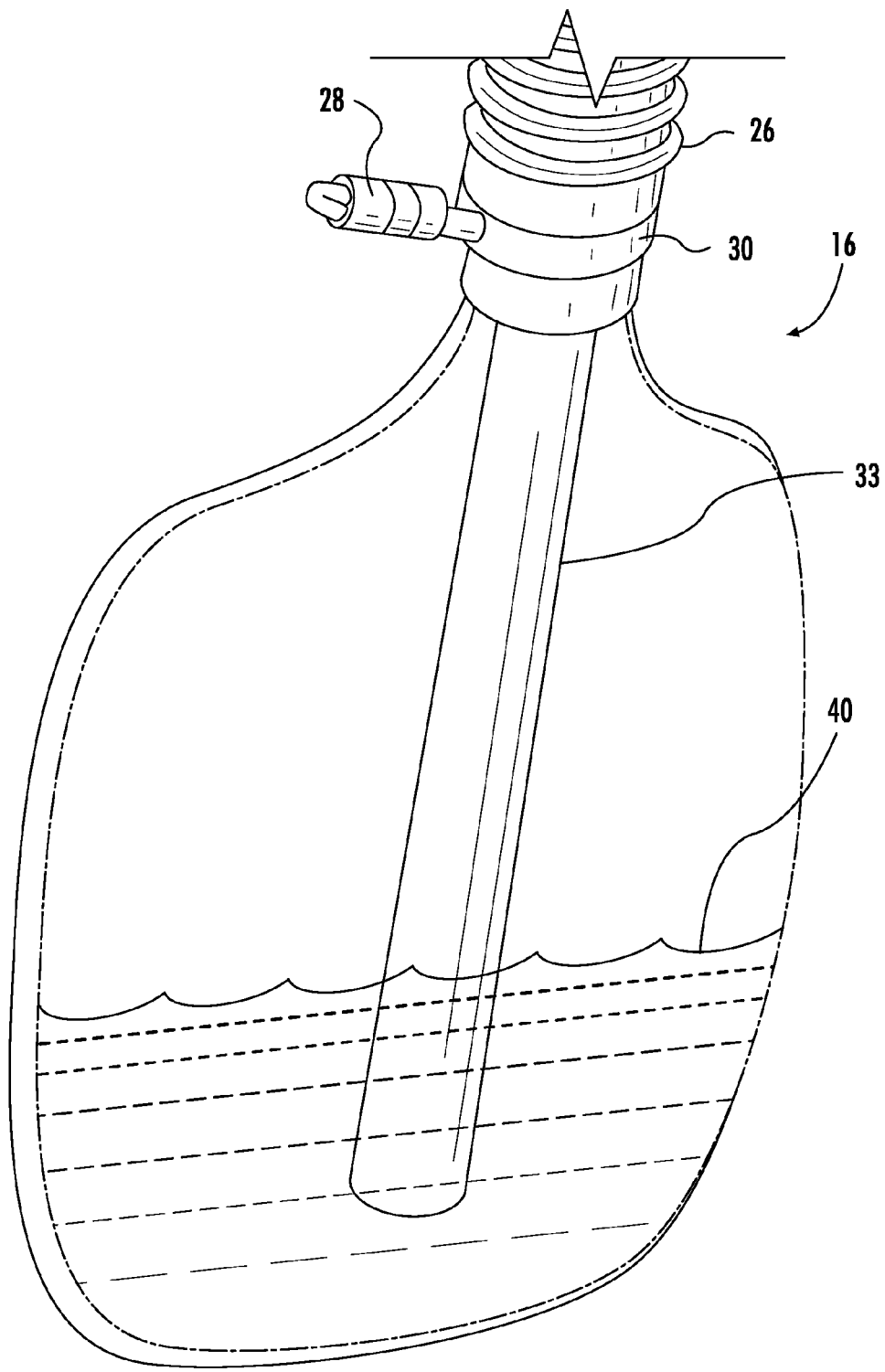
FIG. 11 is a perspective, close up view of the collection bag depicted in FIG. 1, and illustrating, in particular, a distal condensation tube and water that has collected from the wearer's exhalant, according to an embodiment of the technology described herein.

The collection bag 32 is configured to collect a wearer's exhalant as it gathers as vapor within the proximal condensation tube assembly 14, condenses into droplets, and drops into the collection bag as water 40 in liquid form. Collected water 40 in the collection bag 32 is best depicted in FIG. 11. The exhaled vapor collection device 10 is thus configured to collect a wearer's exhalant in the collection bag 32 to provide for later hydration.

Figure 10:
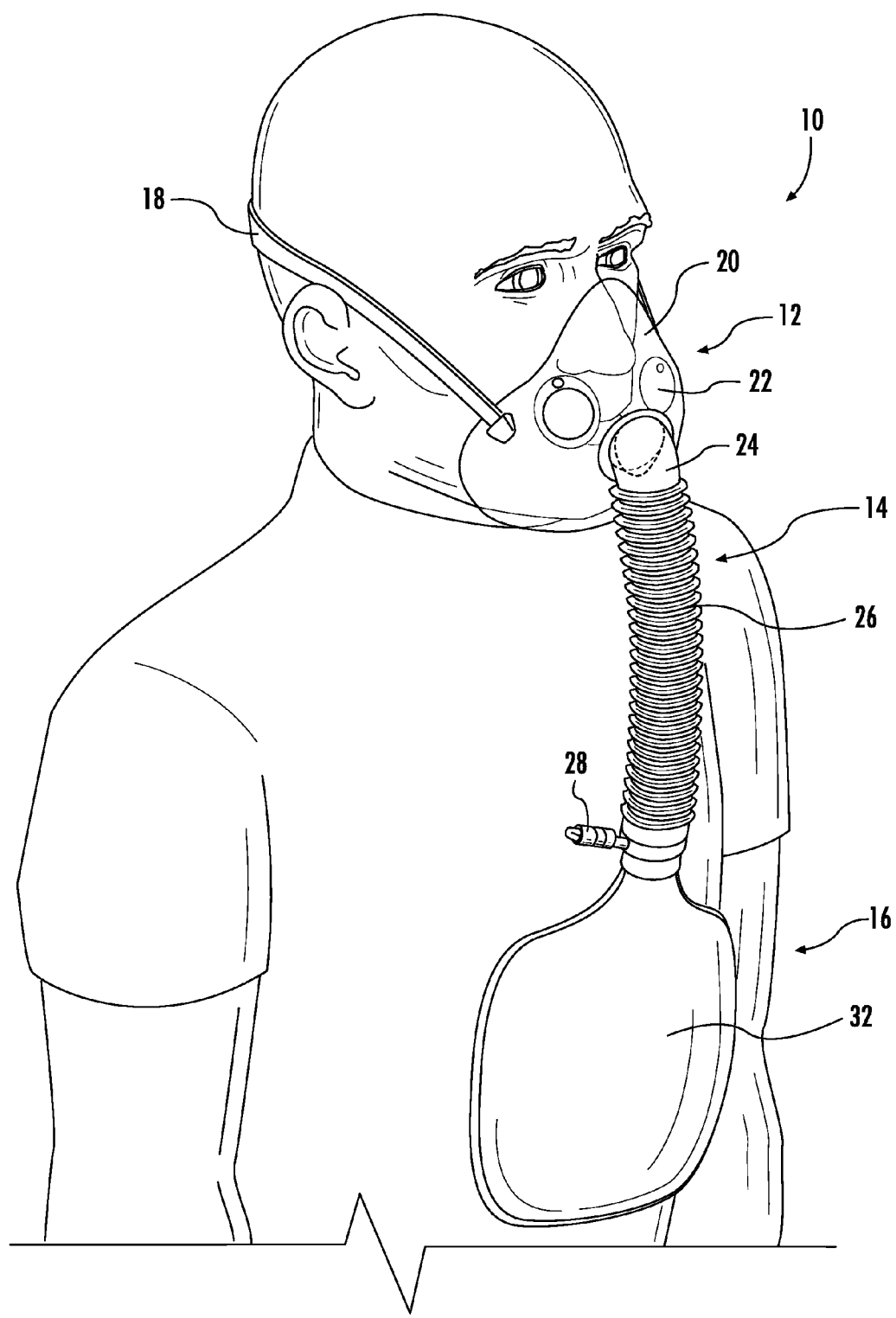
FIG. 10 is a perspective, close up view of the collection bag depicted in FIG. 1, and illustrating, in particular, the device in use on a wearer, according to an embodiment of the technology described herein.

A wearer wearing the exhaled vapor collection device 10 is best depicted in FIG. 10, in which the wearer breathes inwardly with intake air through one-way intake valves 22, exhales outwardly into the facial mask 12 the air exiting through exit port 24 and into the proximal condensation tube assembly 14, where water droplets collect and drain into the collection bag 32.

The exhaled vapor collection device 10 includes a pressure escape valve 28. The pressure escape valve 28 is fluidly coupled to the proximal condensation tube 26 and configured for operative actuation by the wearer to release pressure should pressure build up and need to be released from within the exhaled vapor collection device 10. By way of example, the pressure escape valve 28 can be opened and closed as needed by the wearer.

Figure 3:
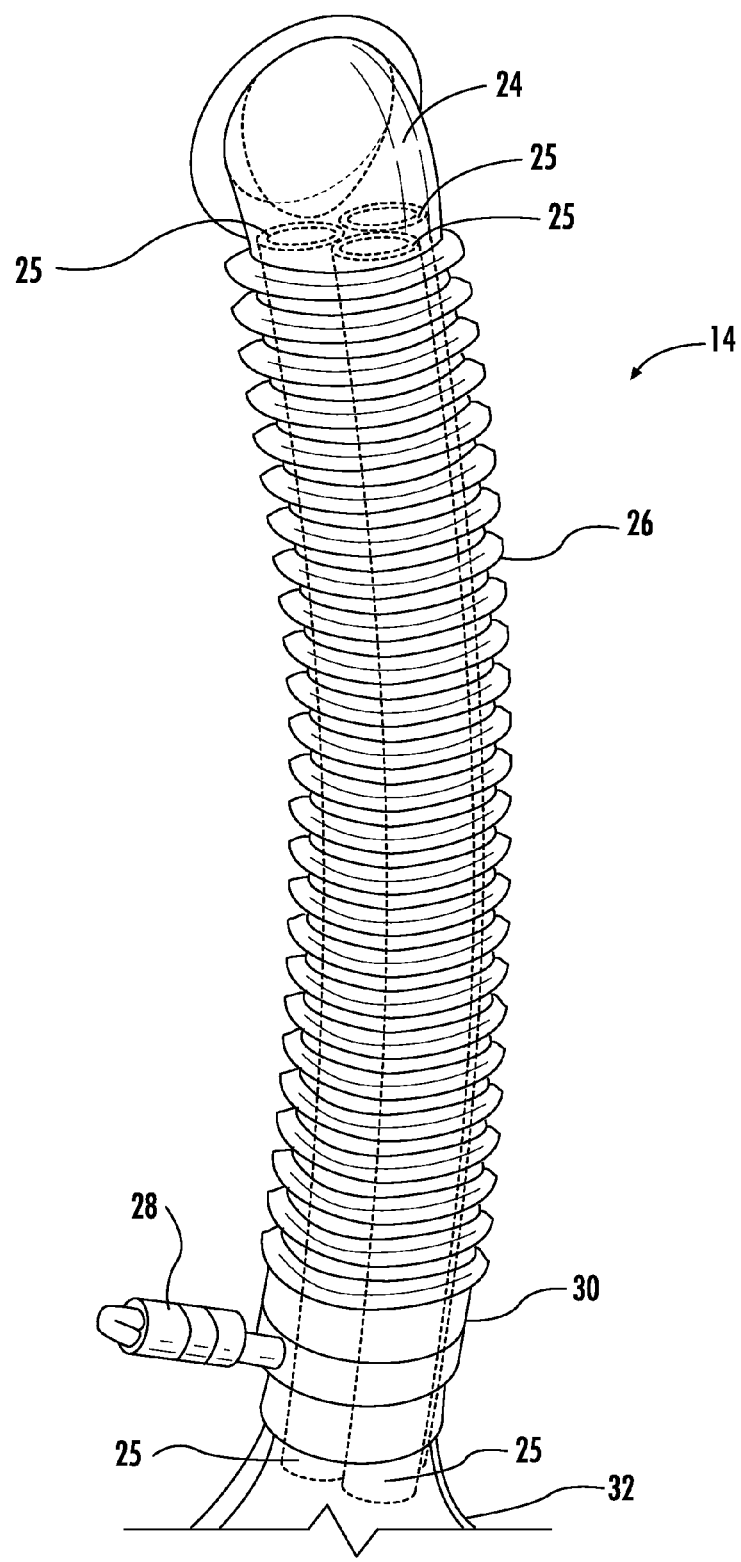
FIG. 3 is a perspective, close up view of the proximal condensation tubes depicted in FIG. 1.

In at least one embodiment, the exhaled vapor collection device 10 includes multiple proximal condensation tubes 25 contained within a larger one 26. In this embodiment, the multiple proximal condensation tubes 25 are fluidly coupled to the exit port 24 of the facial mask 12. Each proximal condensation tube 25 has an interior and exterior surface upon which exhaled vapor collects. The multiple proximal condensation tubes 25 contained within a larger one 26 is best depicted in FIG. 3. This embodiment provides greater surface area, to facilitate greater vapor collection, on which water droplets can collect and drain into the collection bag 32.

In this embodiment, wherein the exhaled vapor collection device 10 includes multiple proximal condensation tubes 25 contained within a larger one 26, the multiple proximal condensation tubes 25 can be made of "cold sticks." Somewhat analogous to chem-sticks, or glow sticks, a cold stick can be temperature neutral until actuation by a user to then create a "cold" stick, much like a glow stick that does not glow until the stick is bent to begin the actuation and create the glow. Such a cold stick can be utilized as item 25 with the large tube 26. At a time of need the user/wearer can activate the cold sticks and place them within large condensation tube 26. As exhaled vapor from the wearer hits the cold stick, condensation of water droplets can occur at an accelerated rate.

The length of the proximal condensation tube assembly 14 can vary. By way of example only, some versions may be twelve inches in length or sixty inches in length, or an intermittent length in between.

Figure 5:
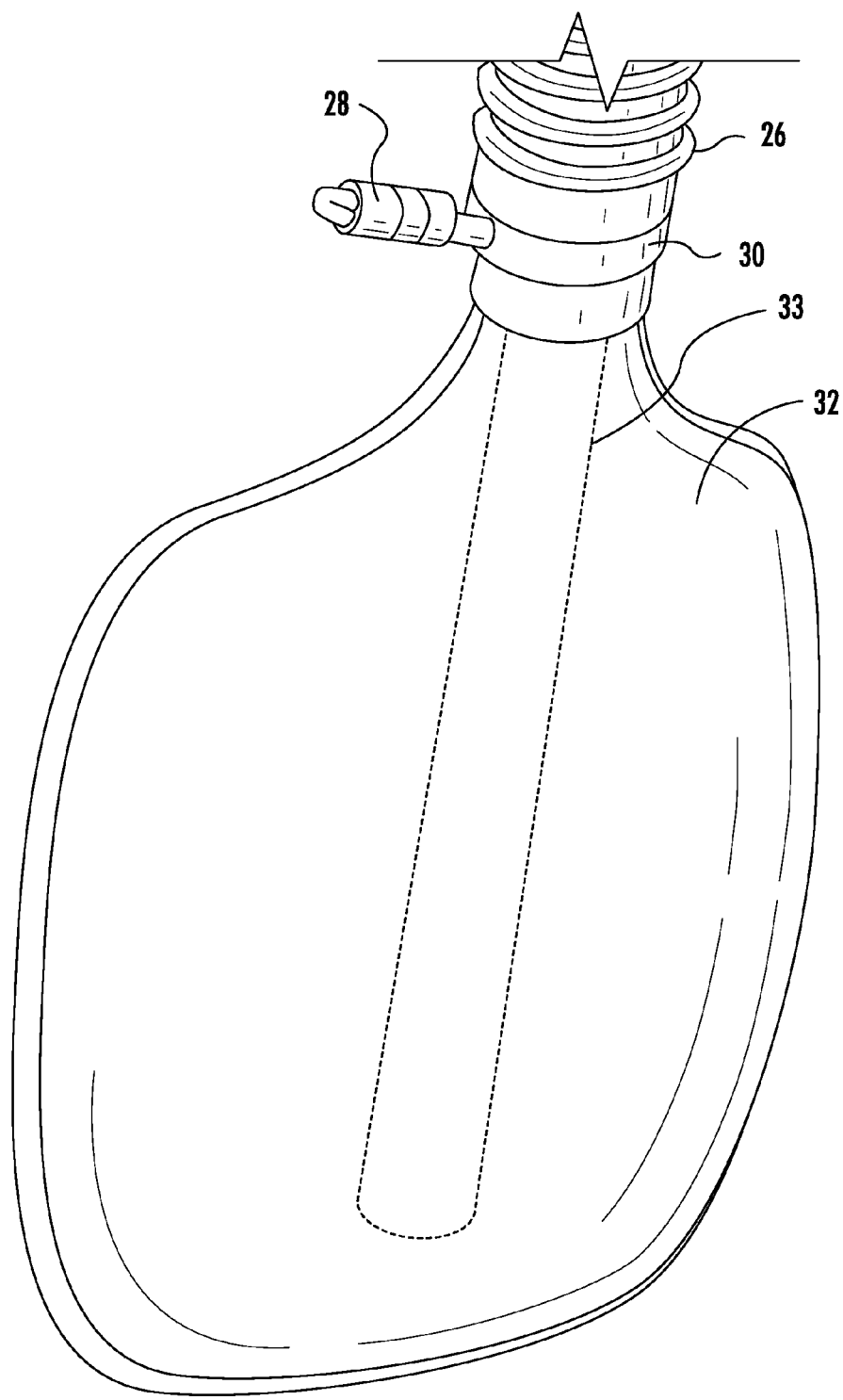
FIG. 5 is a perspective, close up view of the collection bag depicted in FIG. 1, and illustrating, in particular, a distal condensation tube, according to an embodiment of the technology described herein.
Figure 6:
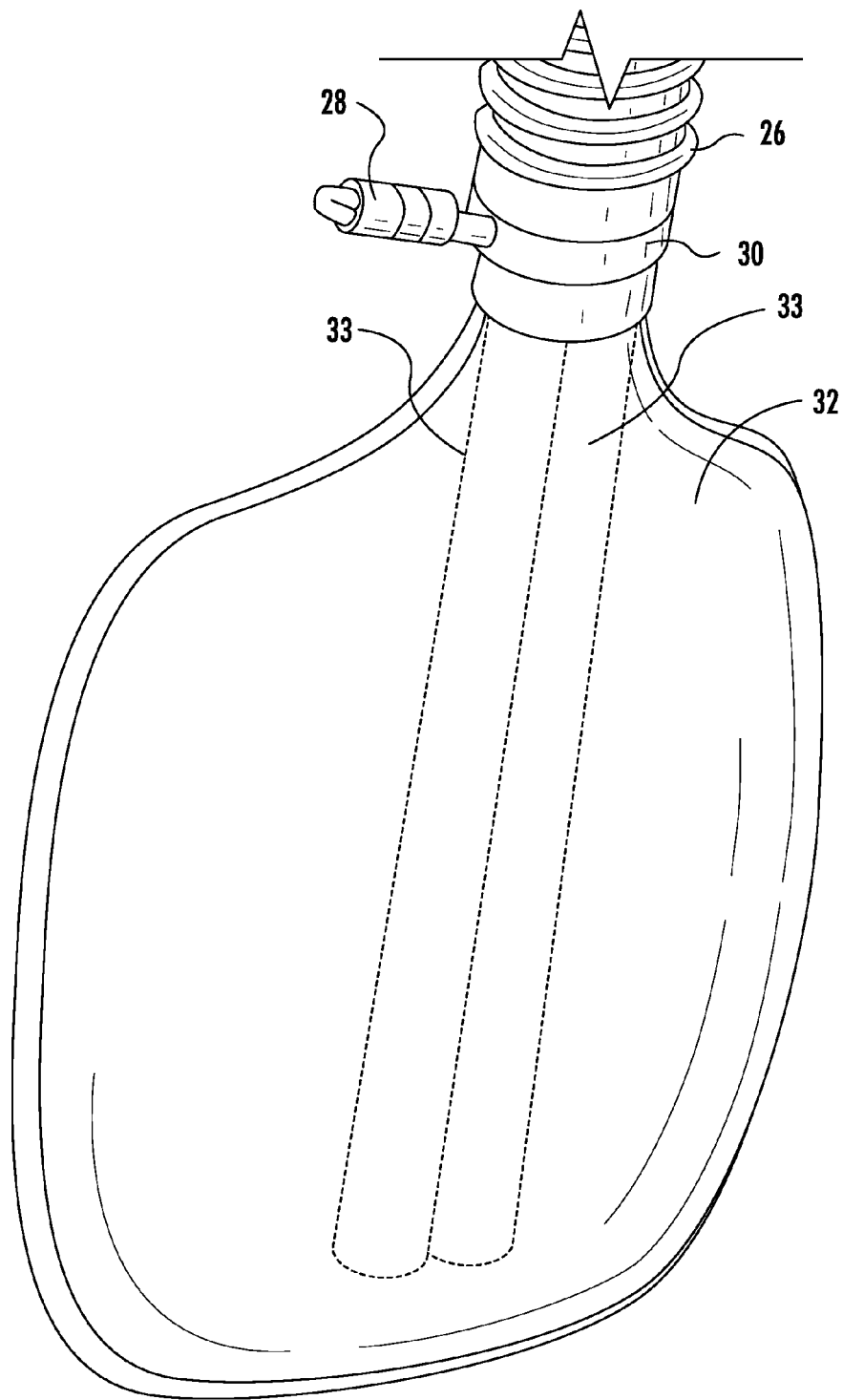
FIG. 6 is a perspective, close up view of the collection bag depicted in FIG. 1, and illustrating, in particular, multiple distal condensation tubes, according to an embodiment of the technology described herein.

In at least one embodiment, the exhaled vapor collection device 10 includes a distal condensation tube 33. As depicted in FIG. 5, for example, the exhaled vapor collection device 10 includes a single distal condensation tube 33. However, in alternative embodiments, the exhaled vapor collection device 10 includes multiple distal condensation tubes 33, as depicted in FIG. 6. Each distal condensation tube 33 is configured to facilitate greater vapor collection. The distal condensation tube 33 is fluidly coupled to the proximal condensation tube 26 to facilitate greater vapor collection. The distal condensation tube 33 is disposed within the collection bag 32 in various embodiments, and as depicted in FIGS. 5 and 6.

Figure 7:
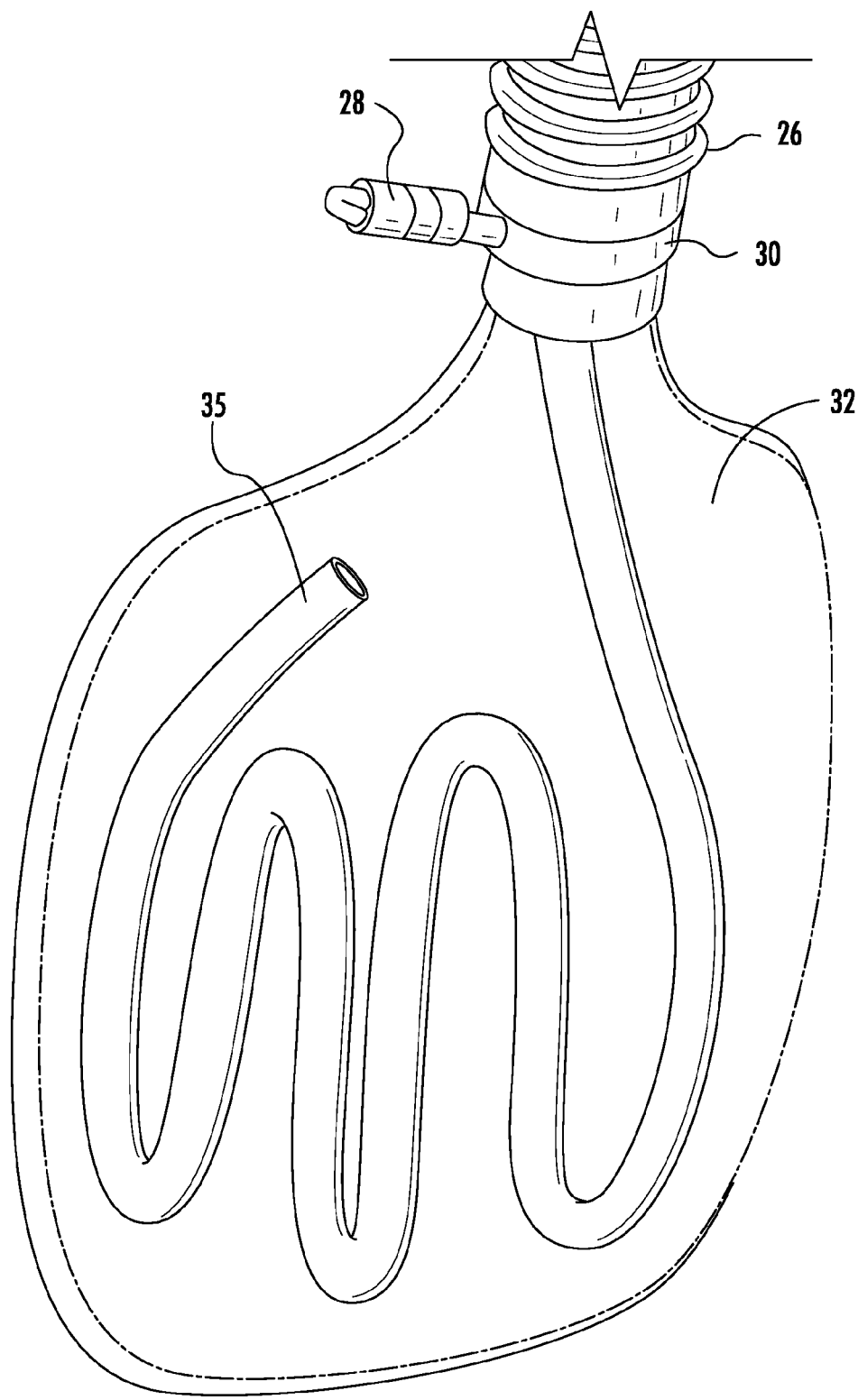
FIG. 7 is a perspective, close up view of the collection bag depicted in FIG. 1, and illustrating, in particular, a lengthened and curved distal condensation tube, according to an embodiment of the technology described herein.

In at least one embodiment, the exhaled vapor collection device 10 includes an elongated distal condensation tube 35. An elongated distal condensation tube 35 is depicted in both FIGS. 7 and 8. The elongated distal condensation tube 35 is configured to facilitate greater vapor collection with a greater tube surface area. In at least one embodiment, the elongated distal condensation tube 35 is disposed with the collection bag 32 and has multiple curves and multiple direction changes within the collection bag 32 to facilitate greater vapor collection.

Figure 8:
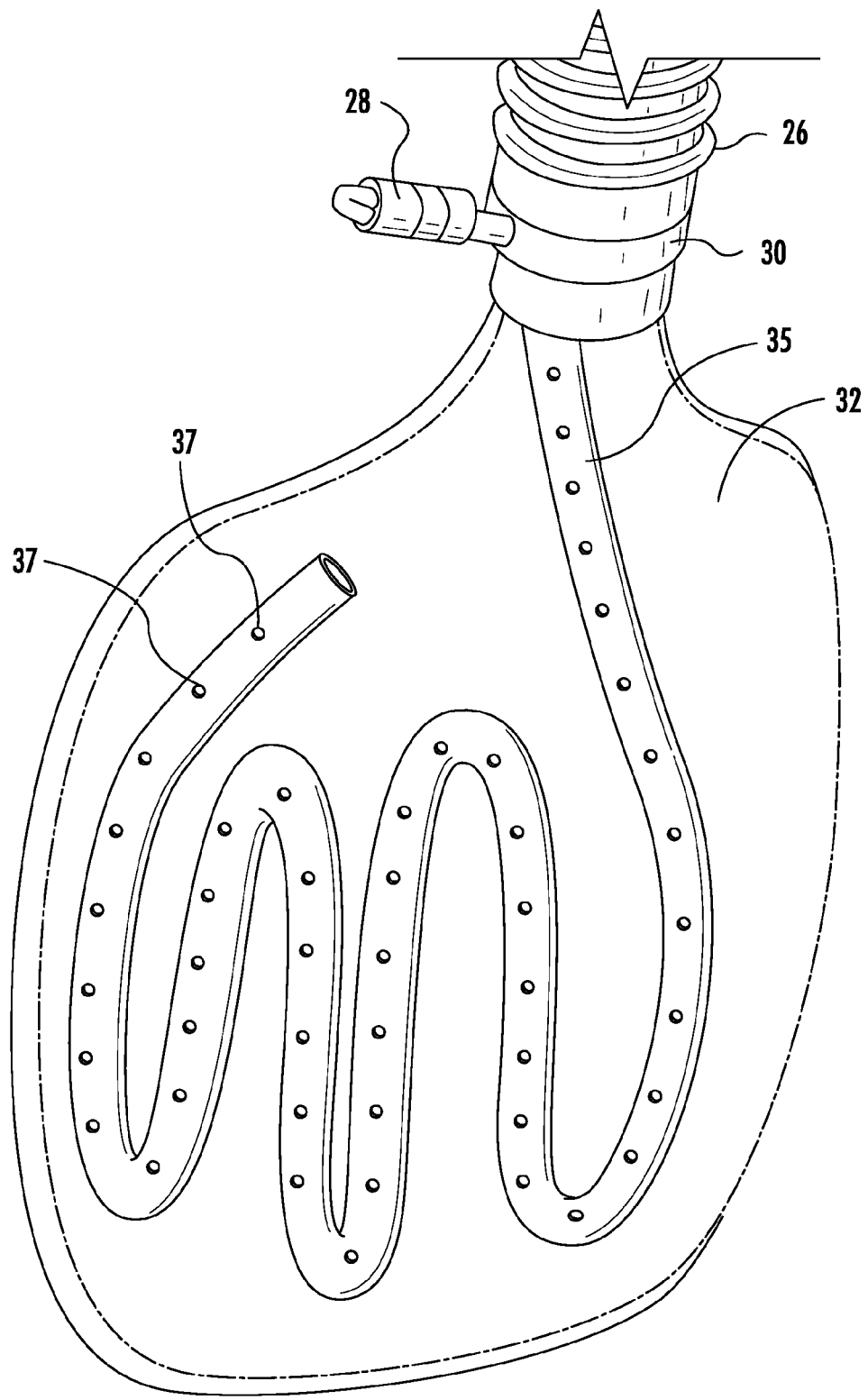
FIG. 8 is a perspective, close up view of the collection bag depicted in FIG. 1, and illustrating, in particular, a lengthened, curved, and perforated distal condensation tube, according to an embodiment of the technology described herein.

In at least one embodiment, the elongated distal condensation tube 35 is configured with multiple pores 37. The multiple pores 37 on the elongated distal condensation tube 35 are best depicted in FIG. 8. The multiple pores 37 are disposed within a surface of the distal condensation tube 33 or elongated distal condensation tube 35 to facilitate greater vapor collection.

Figure 9:
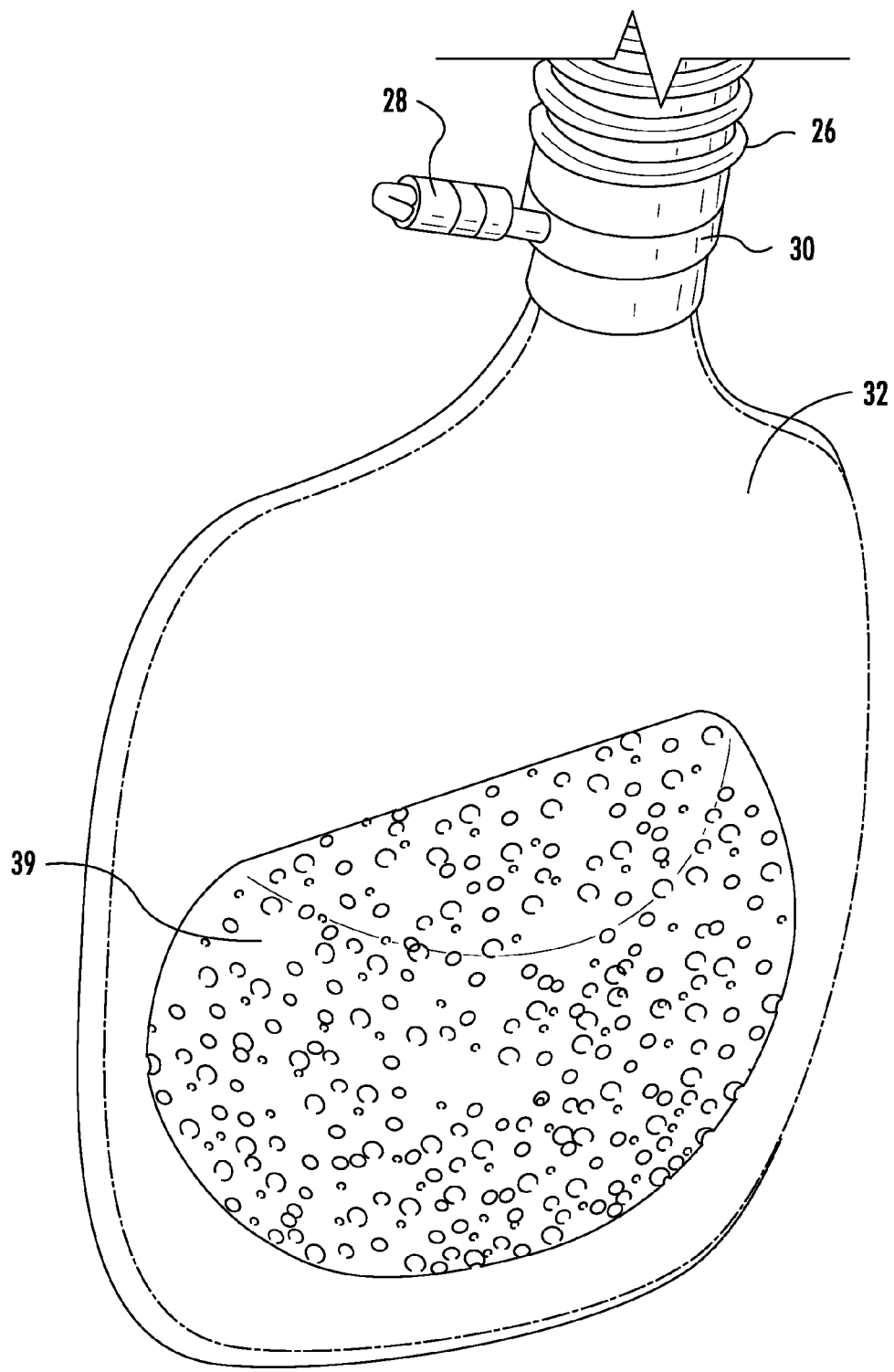
FIG. 9 is a perspective, close up view of the collection bag depicted in FIG. 1, and illustrating, in particular, a sponge disposed within, according to an embodiment of the technology described herein.

In at least one embodiment, the exhaled vapor collection device 10 includes a sponge 39. The sponge 39 is best depicted in FIG. 9. The sponge 39 is disposed within the collection bag 32 to facilitate greater vapor collection. By way of example, in at least one embodiment, the sponge 39 is made of a course plastic material to be used in combination with or instead of condensation tubes. The sponge 39 provides a large surface area and diverse temperature gradients.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. An exhaled vapor collection device to collect a wearer's exhalant to provide for later hydration, the device comprising:
    a facial mask;
    a one-way intake valve disposed within the facial mask and configured to allow the one-way intake of air into the facial mask;
    an exit port disposed within the facial mask and configured to allow the one-way exit of air out from the facial mask;
    a plurality of proximal condensation tubes fluidly aligned in parallel to facilitate greater vapor collection and coupled to the exit port of the facial mask, each proximal condensation tube having an interior surface upon which exhaled vapor collects;
    a collection bag fluidly coupled to the proximal condensation tube to collect a wearer's exhalant; and
    a plurality of distal condensation tubes fluidly coupled to the proximal condensation tube and disposed within the collection bag to facilitate greater vapor collection with a greater tube surface area; and
    wherein the exhaled vapor collection device is configured to collect a wearer's exhalant in the collection bag to provide for later hydration.

2. The exhaled vapor collection device of claim 1, further comprising:
    a pair of one-way intake valves disposed within the facial mask and configured to allow the one-way intake of air into the facial mask.

3. The exhaled vapor collection device of claim 1, further comprising:
    a pressure escape valve fluidly coupled to the proximal condensation tube and configured for operative actuation to release pressure.

4. The exhaled vapor collection device of claim 1, further comprising:
    an elongated distal condensation tube disposed within the collection bag having a plurality of curves and a plurality of direction changes within the collection bag to facilitate greater vapor collection with a greater tube surface area.

5. The exhaled vapor collection device of claim 1, further comprising:
    a plurality of pores disposed within a surface of the distal condensation tube to facilitate greater vapor collection.

6. The exhaled vapor collection device of claim 1, further comprising:
    a sponge disposed with the collection bag to facilitate greater vapor collection.

7. The exhaled vapor collection device of claim 1, further comprising:
    a strap disposed on the facial mask to wrap around a back side of the wearer's head and secure the mask to the wearer over both the nose and the mouth of the wearer.

8. An exhaled vapor collection device to collect a wearer's exhalant to provide for later hydration, the device comprising:
    a facial mask;
    at least one one-way intake valve disposed within the facial mask and configured to allow the one-way intake of air into the facial mask;
    an exit port disposed within the facial mask and configured to allow the one-way exit of air out from the facial mask;
    a plurality of proximal condensation tubes aligned in parallel to facilitate greater vapor collection and fluidly coupled to the exit port of the facial mask, each proximal condensation tube having an interior surface upon which exhaled vapor collects;
    a collection bag fluidly coupled to the at least one proximal condensation tube to collect a wearer's exhalant; and
    at least one distal condensation tube disposed within the collection bag to facilitate greater vapor collection;
    wherein the exhaled vapor collection device is configured to collect a wearer's exhalant in the collection bag to provide for later hydration.

9. The exhaled vapor collection device of claim 8, further comprising:
    a distal condensation tube fluidly coupled to the proximal condensation tube and disposed within the collection bag to facilitate greater vapor collection with a greater tube surface area.

10. The exhaled vapor collection device of claim 8, further comprising:
    a plurality of distal condensation tubes fluidly coupled to the proximal condensation tube and disposed within the collection bag to facilitate greater vapor collection with a greater tube surface area.

11. The exhaled vapor collection device of claim 8, further comprising:
    a plurality of pores disposed within a surface of the at least one distal condensation tube to facilitate greater vapor collection.

12. The exhaled vapor collection device of claim 8, further comprising:
    an elongated distal condensation tube disposed within the collection bag having a plurality of curves and a plurality of direction changes within the collection bag to facilitate greater vapor collection with a greater tube surface area.

13. An exhaled vapor collection device to collect a wearer's exhalant to provide for later hydration, the device comprising:
    a facial mask;

a strap disposed on the facial mask to wrap around a back side of the wearer's head and secure the mask to the wearer over both the nose and the mouth of the wearer;

a pair of one-way intake valves disposed within the facial mask and configured to allow the one-way intake of air into the facial mask;

an exit port disposed within the facial mask and configured to allow the one-way exit of air out from the facial mask;

a plurality of proximal condensation tubes fluidly coupled to the exit port of the facial mask, each proximal condensation tube having an interior surface upon which exhaled vapor collects;

a collection bag fluidly coupled to the condensation tube to collect a wearer's exhalant;

a plurality of distal condensation tubes fluidly coupled to the proximal condensation tube and disposed with the collection bag to facilitate greater vapor collection with a greater tube surface area;

a pressure escape valve fluidly coupled to the proximal condensation tube and configured for operative actuation to release pressure;

wherein the exhaled vapor collection device is configured to collect a wearer's exhalant in the collection bag to provide for later hydration.

14. The exhaled vapor collection device of claim 13, further comprising:

a sponge disposed within the collection bag to facilitate greater vapor collection.

* * * * *